United States Patent [19]

Grollier

[11] Patent Number: 4,796,812
[45] Date of Patent: Jan. 10, 1989

[54] DEVICE FOR PREPARING AND DISPENSING A PRODUCT CONSISTING OF TWO COMPONENTS AND THE CORRESPONDING PROCESS

[75] Inventor: Jean-Francois Grollier, Paris, France

[73] Assignee: L'Oreal, Paris, France

[21] Appl. No.: 29,539

[22] Filed: Mar. 24, 1987

[30] Foreign Application Priority Data

Mar. 24, 1986 [LU] Luxembourg ............................ 86368

[51] Int. Cl.⁴ ................................................ B05B 7/26
[52] U.S. Cl. .................... 239/303; 239/310; 239/311; 239/315; 239/316; 239/343; 422/236
[58] Field of Search ................ 239/303, 304, 306–308, 239/310, 311, 315, 316, 326, 343, 370, DIG. 23; 422/236, 238

[56] References Cited

U.S. PATENT DOCUMENTS

| 1,973,319 | 9/1934 | Nelson | 239/316 X |
| 2,862,765 | 12/1958 | Wing | 239/303 |
| 3,235,126 | 2/1966 | Shay . | |
| 3,355,071 | 11/1967 | Jordan | 239/316 X |
| 3,809,084 | 5/1974 | Hansen | 239/315 X |

FOREIGN PATENT DOCUMENTS

| 4717 | 6/1932 | Australia | 239/315 |
| 2195917 | 3/1974 | France . | |
| 2536993 | 6/1984 | France . | |
| 696648 | 10/1965 | Italy | 239/307 |
| 2024049 | 1/1980 | United Kingdom . | |

*Primary Examiner*—Douglas C. Butler
*Assistant Examiner*—Mary Beth O. Jones
*Attorney, Agent, or Firm*—Cushman, Darby & Cushman

[57] ABSTRACT

A device for preparing and dispensing a product consisting of two components which may be mixed only when the product is being dispensed, one of the components being fluid and said components being packaged in a pressurized container for dispensing in the form of foam through the outlet valve of the pressurized container, while the other component is solid and is placed outside said pressurized container, wherein the valve is controlled by the user by means of an operating device which comprises an ejection duct, and wherein a chamber whose outlet is closed by a grid is arranged onto that end of the ejection duct which is remote from the valve, said chamber enclosing the solid component in particulate form.

14 Claims, 1 Drawing Sheet

*4,796,812*

DEVICE FOR PREPARING AND DISPENSING A PRODUCT CONSISTING OF TWO COMPONENTS AND THE CORRESPONDING PROCESS

FIELD OF THE INVENTION

The present invention relates to a device for preparing and dispensing a product consisting of two components, which may be mixed only when the product is dispensed; it also relates to a process for preparing and dispensing a product consisting of two components. Generally the mixture of these components should only be produced at the time of dispensing, either because it cannot be stored because of a relatively fast chemical reaction, or because it should be used as soon as it is produced. The components of a product of this kind are usually stored in separate packages, the mixture being produced only at the last moment and in accordance with the final quantity required.

PRIOR ART

In the particular case where one of the components is fluid, while the other is solid, U.S. Pat. No. 3,355,071 has already proposed a device permitting the separate storage of the fluid component and of the solid component, the fluid component being dispensed from a pressurized container through a perforated solid block, the passage of the fluid through the said block enabling the solid to be entrained in the fluid stream. This device is proposed for imparting a colour to a foam dispensed by an aerosol container and the perforated solid block can be interchanged to make it possible to alter the colour of the dispensed foam. However, the passage of the foaming product into the channel provided in the middle of the solid block permits only a minor entrainment of solids by the ejected foam and this entrainment is generally minor; in addition, in proportion to the wear of the block, the quantity of solid which is entrained by the foam is not constant.

OBJECTS OF THE INVENTION

It is an object of the invention to provide a device which makes is possible to produce, in a reliable, uniform and reproducible manner, the mixture of a solid component and a fluid component which is dispensed in the form of a foam. It is a further object of the the invention to arrange the solid component in particulate form in the ejection path of the fluid component. The fact that a solid component is present in a divided form enables the entrainment of the solid component by the fluid component to be considerably increased and ensures the uniformity of the entrainment with time. It is clear that the device according to the above-mentioned U.S. Pat. No. 3,355,071 does not permit the use of a solid component in a particulate form in any event, because in a device of this kind nothing would make it possible to hold back the particles which would all be ejected as soon as the foam dispensing commenced. It is a further object of the invention to package the solid component in particulate form inside a chamber closed by a grid, the grid enabling the solid particles to be held back while allowing the fluid component to pass through. If the solid particles have a mean diameter which is smaller than the mesh opening of the grid, the grid may be employed as a mechanical support for a fibrous plug which holds back the solid particles and allows the foam to pass through, the said plug being placed against the grid inside the chamber containing the solid particles.

It has already been proposed, for example in British Patent Application No. 2,024,049, to dispense through a grid, in the form of foam, a liquid product capable of generating a foam. However, a device of this kind is provided only for dispensing a liquid component without there ever being any suggestion of the use of the liquid stream to entrain a solid component; in addition, the liquid which is conveyed onto the grid is ejected from a container by means of a manual pump, so that this liquid is converted into foam only on passing through the grid.

It is therefore a further object of the invention for the fluid component to be dispensed to be ejected from a pressurized container, in the form of foam. The specialist would not be led in any way to employ a grid of the type of that described in British Pat. No. 2,024,049, since, in the case of the present invention, the foam is to be already formed when it arrives in the chamber containing the particulate solid.

In addition, Applicant's assignees have found that it is advantageous to adopt both a particular size of the grid closing the chamber of the device and particular characteristics of the foam injected into the chamber, both as regards its structure and as regards its flow rate.

SUMMARY OF THE INVENTION

The present invention therefore provides a device for preparing and dispensing a product consisting of two components which may be mixed only when the product is being dispensed, one of the components being fluid and said components being packaged in a pressurized container for dispensing in the form of foam through the outlet valve of the pressurized container, while the other component is solid and is placed outside said pressurized container, wherein the valve is controlled by the user by means of an operating device which comprises an ejection duct, and wherein a chamber whose outlet is closed by a grid is arranged onto that end of the ejection duct which is remote from the valve, said chamber enclosing the solid component in particulate form.

In a preferred embodiment, the grid has from 6 to 100 meshes per centimetre and a mesh opening of between 0.1 and 1.5 millimeters, preferably 0.2 to 1 millimeter and more particularly approximately 0.8 millimeters, the foam emerging from the container having a compactness index of between 3 and 60 s, preferably between 3 and 40 s, and being discharged into the chamber so as to produce, on the grid, an output of between 0.8 and 3 g/cm$^2$/s, and more particularly between 1 and 2 g/cm$^2$/s.

The grid may be made of plastic or expanded metal, for example expanded aluminium. In this case the meshes of the grid are lozenge-shaped and, depending on their orientation, the number of meshes per cm is thus greater or smaller. It may, for example, in one embodiment be from 5 to 12.

In the present description and claims the compactness index of a foam means the result of the measurement carried out as follows: the foam to be tested is sucked into a cylindrical test tube 1.2 cm in diameter and 25.3 cm high; a steel ball 9.5 mm in diameter and weighing 3.51 g is placed on the surface of the foam without any initial velocity, and the time taken by this ball to fall in the foam over a height of 23.5 cm is measured in seconds. The measured time constitutes the compactness index of the foam within the meaning of the present patent application.

In a preferred embodiment of the invention, the chamber which carries the grid is bounded by a side wall which widens gradually outwards from the ejection channel to the grid; the side can then enclose the particulate solid intended for a single measured quantity and it is changed by the user after each dispensing of a measured quantity of fluid product. There may be a whole series of chambers containing different solids chosen by the user, according to his or her needs.

More than 80% of the particles of which the solid component consists preferably have a diameter of between 0.005 and 1.0 mm. As already indicated, when the solid particles are sufficiently large not to pass through the meshes of the grid, then the grid can be used solely to hold back the solid component. On the other hand, in the case where the solid particles would be liable to pass too easily through the grid at the time when the foam is being dispensed, provision may advantageously be made for the particulate solid component to be separated from the grid by a retaining plug which is insoluble in the fluid component, this plug being permeable to the said fluid component and having a specific density of between 20 and 150 kg/m$^3$. This plug may be fibrous and nonwoven; it may also consist of an open-cell foam.

The propellant gas employed in the pressurized container employed for storing the fluid component can advantageously be an alkane such as propane, butane or mixtures thereof, or alternatively at least one halogenated, chlorinated and/or fluorinated and nonhydrolysable hydrocarbon such as the compounds sold under the Trade Mark "Freon" by the company Du Pont de Nemours.

Understandably, it is advantageous to make use of the device according to the present invention each time it is intended to produce and employ a composition whose components are incompatible, unstable or reactive or do not store well in each other's presence. The device according to the invention has a preferred application in the field of cosmetics and of dermo-pharmacy. This device can thus be employed for preparing and dispensing dyes, lightening shampoos, dyeing shampoos, conditioning shampoos or oils, for example for seborrhoeic or dandruff conditions, restructuring compositions for hair, compositions for treating acneform or seborrhoeic conditions of the skin or dermatoses, compositions for colouring the skin or for actinic protection.

The device according to the present invention makes it possible to apply to hair a foam intended either to lighten the hair or to colour it in a range of shades which can vary depending on the nature and on the quantity of the component present in the chamber.

According to a particular application of the device of the invention, the fluid component is a dyeing or a hair shampoo composition, and the solid component is a powder of at least one oxidizing compound for hair.

When the final product is a shampoo intended to affect the colour of hair, the container encloses, as a fluid component, a foaming aqueous composition as well as the ingredients which are usually employed for an application of this type. The pH of this fluid component varies from 8 to 12. For a slightly bleaching shampoo, the pH is close to 9 and is adjusted by means of an aliphatic or hydroxyaliphatic amine such as, for example, monoethanolamine. In the case of a bleaching or dyeing shampoo, the pH is approximately 10 and is adjusted by means of an aqueous ammonia solution. The sole chamber in these three examples contains, as component, a peroxide in solid form, such as powdered urea peroxide. Examples 1 to 3 below relate to this type of application.

According to another application of the invention, the fluid component is a solution of hair dyes, and the solid component is a mordanting or oxidation product. This device enables, for example, hair to be dyed by mordanting using natural dyes in the presence of metal salts of metals of groups II to V and, preferably, aluminium salts or complexes or the salts described in the document EP-A-133,129; the natural dyes are, for example, those described in EP-A-133129, especially brasilin and haematoxylin. In an application of this kind the pressurized container encloses an acidic aqueous solution or dispersion of the natural dye in the presence of known adjuvants, while the chamber contains the metal salt in particulate solid form.

According to yet another application, the fluid component is a solution of cosmetic polymer and the solid component is a mono- or dimethylol of urea or of thiourea or of derivatives thereof, capable of being used as a hair restructuring agent.

It is also possible to package a basic solution in the pressurized container and a solid acid product in the chamber, such as tartaric acid or citric acid; or, conversely, to package an acidic, optionally oxidizing solution in the container and a basic solid product in the chamber, for example an alkali metal hydroxide or carbonate. An acidic oxidizing solution may consist of an aqueous solution of hydrogen peroxide.

It is also possible to package a reducing solution in the pressurized container and an oxidizing powder in the chamber, and this makes it possible to produce an exothermic redox reaction. It is also possible to package an oxidizing solution in the container and a reducing powder in the chamber.

The invention relates particularly to the use of the device specified above for the treatment of hair, of the scalp or of the skin.

The present invention also provides a process for preparing and dispensing a product consisting of two components which may be mixed only when the product is being dispensed, one of the components being fluid, packaged in a pressurized container and dispensed in the form of foam through the outlet valve of the pressurized container, while the other component is solid and placed outside the pressurized container, the valve being controlled by the user by means of an operating device which comprises an ejection channel, characterized in that a chamber whose outlet is closed by a grid is arranged on that end of the ejection channel which is remote from the valve, and in that the solid component is placed in particulate form in the chamber.

BRIEF DESCRIPTION OF THE DRAWINGS

In order that the invention may be better understood, a description will now be given, by way of a purely illustrative example without implying any limitation, of an embodiment shown in the attached figures and a number of methods of application, wherein.

DESCRIPTION OF THE PREFERRED EMBODIMENT

Figure 1:
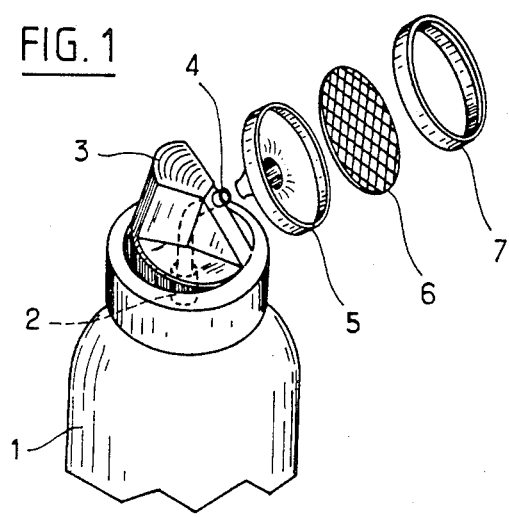
FIG. 1 is a perspective exploded view of the element of the present invention.

The device shown in the FIG. 1 comprises a container 1 of the aerosol can type enclosing a liquid component and a propellant gas. The outlet of this container comprises a dispensing valve 2 associated with an operating device 3; the operating device 3 is a push-button whose ejection channel 4 terminates, at its end remote from that which receives the valve 2, in a projecting nozzle. A chamber 5 is fastened on the projecting nozzle of the ejection channel 4.

The chamber 5 is funnel-shaped; its narrow end is fitted onto the ejection channel 4; its wide end is closed by a grid 6 held in position on the side wall of the chamber 5 by virtue of a snap-fastening collar 7. The grid 6 consists of a fine-meshed metal cloth perpendicular to the fluid stream delivered by the container 1. The surface area of the grid 6 is substantially equal to 80 times the perpendicular cross-section of the outlet of the ejection channel 4.

A device of this kind permits a fluid component and a solid component to be mixed in the desired quantities. In fact, the container encloses the fluid component, that is to say a fluid in which the propellant gas employed is partially dissolved with the result that the fluid component leaves the ejection channel 4 in the form of foam, the foam being formed spontaneously by the liquid ejected at the moment of decompression by vaporisation of the dissolved propellant. The chamber 5 contains the solid component in particulate form. When the pushbutton is pressed to actuate the valve 2, the fluid component in the form of foam is conveyed into the chamber 5 where it mixes with the solid component; depending on the size of the particles, entrainment of the particles by the foam may take place through the grid, where the particles may be gradually dissolved by the composition of which the foam consists; a product resulting from the mixing of the fluid component contained in the container 1 and of the solid component contained in the chamber 5 is thus produced.

Figures 2, 3:
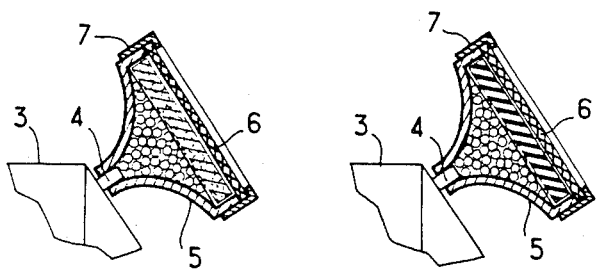
FIG. 2 is a sectional view showing another embodiment of the present invention.
FIG. 3 is a view similar to FIG. 2 and showing a third embodiment of the present invention.

In the case of the example described, the grid 6 has 12 meshes per centimeter, the mesh opening being 0.8 mm; the diameter of the particles may, in the case of more than 80% of these, be about 0.4 mm. If a mean diameter of less than 0.4 mm were adopted, to prevent the particulate solid from passing through the grid during use, a retaining plug as shown in FIG. 2 would be placed in the chamber 5, against the grid 6; this plug may consist of nonwoven synthetic fibres having a sufficient density to prevent the loss of solid particles before the dispensing operation; in this case, the retaining plug would advantageously have a specific density of 20 to 24 kg/m$^3$. The retaining plug could, alternatively, consist of an open-cell plastic as shown in FIG. 3.

In order to control the quantity of solid component which is mixed with the fluid component, it is possible to modify the particle size distribution of the solid component, its quantity and its distribution in the chamber 5. When the mixture results in colouration, the ratio of the mixture may be supervised visually by inspection of the colour of the dispensed product.

The device just described enables different types of products to be employed and a number of examples of application will be given below.

EXAMPLE 1

A slightly lightening foam shampoo is prepared by introducing 120 g of the following composition into the container:

| | |
|---|---|
| Triethanolamine laurylsulphate (active substance) | 20 g |
| Lauric diethanolamide (active substance) | 6 g |
| Monoethanolamine | q.s. pH = 9.5 |
| Camomile glycol extract | 4 g |
| Preservative, perfume | q.s. |
| Water | q.s. 100 g |

After crimping the valve 2 in place, 2 g of a 43/57 mixture of dichlorotetrafluoroethane and of dichlorodifluoromethane are introduced through the valve.

The chamber 5 contains 0.8 g of powdered urea peroxide.

The powder present in the chamber 5 has the following characteristics:
granule diameter of between 0.2 mm and 1 mm;
more than 80% by weight of the granules have a mean diameter of between 0.3 mm and 0.6 mm;
the grid 6 has 12 meshes per centimeter, the mesh opening being 0.8 mm.

This device makes it possible to deliver directly onto wet and unwashed hair a foam with which the hair is impregnated by working in. The foam is left to act for 10 to 15 minutes and is then rinsed off with water.

After washing, rinsing and drying the hair, initially dark blonde, acquires a luminous golden blond highlight.

Successive application of this foam lighten the dark blond hair to a golden light blond shade.

EXAMPLE 2

A lightening foam shampoo is prepared by introducing 40 g of the following composition into the container 1 of the device according to the invention:

| | |
|---|---|
| Oleic acid (active substance) | 5.65 g |
| Nonylphenol oxyethylenated with 4 moles of ethylene oxide (active substance) | 7.50 g |
| Nonylphenyl oxyethylenated with 9 moles of ethylene oxide (active substance) | 5.00 g |
| Propoylene glycol | 3.75 g |
| Lauric diethanolamide (active substance) | 5.00 g |
| Cationic polymer (active substance) described and prepared according to French Patent No. 2,270,876, consisting of recurring repeat units of formula: | 1.10 g |

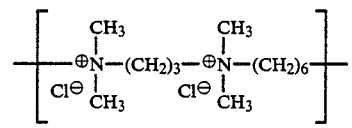

| | |
|---|---|
| Ethyl alcohol | 13.00 g |
| NH$_4$OH (containing 20% of ammonia gas) | 4.00 g |
| Monoethanolamine q.s. pH = | 10.2 |
| Preservative, perfume, sequestering agent q.s. | |
| Water q.s. | 100.00 g |

After crimping, 4 g of a 43/57 mixture of dichlorotetrafluoroethane and of dichlorodifluoromethane are then introduced through the valve.

3.3 g of powdered urea peroxide are introduced into the chamber 5.

The powder present in the chamber 5 has the following characteristics:
granule diameter of between 0.2 mm and 1 mm;
more than 80% by weight of the granules have a diameter of between 0.3 mm and 0.6 mm;
the grid 6 has 12 meshes per centimeter, the mesh opening being 0.8 mm.

This device makes it possible to deliver directly onto wet and unwashed hair a foam with which the hair is impregnated. It is left to act for 20 minutes, and a water rinse is then applied, followed by drying.

After washing, rinsing and drying, natural hair which is initially dark blond is lightened by two shades to a golden blond shade.

EXAMPLE 3

A dyeing shampoo is prepared by introducing 40 g of the following composition into the container 1 of the device:

| | |
|---|---|
| Sodium alkyl ether sulphate (active substance) | 3.450 g |
| Crosslinked polyacrylic acid (active substance) sold under the trade name of "Carbomer 934" by the Goodrich company | 1.000 g |
| Glycol distearate (active substance) | 1.000 g |
| Lauric diethanolamide (active substance) | 1.750 g |
| Resorcinol (active substance) | 0.064 g |
| 1-Amino-4-hydroxybenzene (active substance) | 0.300 g |
| 1,4-Diaminobenzene (active substance) | 0.235 g |
| Meta-aminophenol (active substance) | 0.0215 g |
| 2-Methyl-5-N—$\beta$-hydroxyethyl-aminophenol | 0.445 g |
| Ammonium thiolactate | 0.400 g |
| 4-N—methylaminophenol sulphate | 0.110 g |
| NH$_4$OH (containing 20% of ammonia gas) | 6.450 g |
| Preservative, perfume, sequestering agent | q.s. |
| Water | q.s. 100.000 g |

The pH of this composition is 10.

After crimping, 4 g of a 43/57 mixture of dichlorotetrafluoroethane and of dichlorodifluoromethane are introduced through the valve.

3.3 g of powdered urea peroxide are introduced, as before, into the chamber 5.

The powder present in the chamber 5 has the following characteristics:
granule diameter of between 0.2 mm and 1 mm;
more than 80% by weight of the granules have a diameter of between 0.3 mm and 0.6 mm;
the grid 6 has 12 meshes per centimetre, the mesh opening being 0.8 mm.

This device makes it possible to deliver directly onto wet and unwashed hair a thick and compact foam with which the hair is impregnated. It is left to act for half an hour before rinsing with water is carried out.

After washing, rinsing and drying, the initially 90% white hair is golden mahogany dark blond-coloured.

Examples 4 and 5 which follow illustrate the fact that the device according to the present invention also makes it possible to prepare and dispense hair-restructuring compositions which are not followed by rinsing. In this case, the container 1 contains an aqueous or aqueous alcoholic solution and an acidic catalyst chosen from inorganic or organic acids and acidic salts which may be used in cosmetics, as well as conventional cosmetic adjuvants including polymers such as, for example, vinylpyrrolidone-based copolymers. The chamber 5 contains, for example, powdered dimethylolethylenethiourea.

EXAMPLE 4

A restructuring foam for spoilt hair is prepared by introducing the following composition into the container 1 of the device according to the invention:

| | |
|---|---|
| Quaternized vinylpyrrolidone/dimethylaminoethyl methacrylate copolymer with a molecular weight of 1,000,000, sold at 20% strength of active substance by the General Aniline company under the trade name "Gafquat 755" (active substance) | 0.4 g |
| Tartaric acid | q.s. pH 2.7 |
| Preservative, perfume | q.s. |
| Water | q.s. 100.0 g |

After crimping, 10 g of a 43/57 mixture of dichlorotetrafluorethane and dichlorodifluoromethane are introduced through the valve.

Chamber 5 contains 1.5 g of powdered dimethylolethylenethiourea.

The powder present in the chamber 5 has the following characteristics:
particle diameter of between 0.08 mm and 0.5 mm;
more than 80% by weight of the particles have a diameter of between 0.1 mm and 0.3 mm.

A retaining plug consisting of a sheet of non-woven synthetic fibres with a thickness of 2 mm is placed against the grid 6. This sheet is constituted of fibres having a diameter of about 0.1 mm and density is about 125 Kg/m$^3$.

This device makes it possible to dispense directly a foam with which clean, roughly dried hair is impregnated. The hair is then set; the result is shiny hair which disentangles easily.

EXAMPLE 5

A restructuring foam for natural hair is prepared, using the same composition as that of Example 4, but replacing "Gafquat 755" with 1.5 g (active substance) of vinylpyrrolidone/vinyl acetate copolymer. The contents of chamber 5 and the grid 6 are identical with those of Example 4. A foam is obtained which is applied to clean, roughly dried hair. The hair is set. After drying, the hair shines and the hairdo has body.

EXAMPLE 6

A hair dye employing mordanting with a natural dye is prepared by introducing 60 g of the following composition into the container 1 of the device:

| | |
|---|---|
| Haematoxylin (active substance) | 0.5 g |
| Sodium alkyl ether sulphate (active substance) | 10.0 g |
| Ethyl alcohol | 10.0 g |
| Perfume, preservative | q.s. |
| Water | q.s. 100.0 g |

The pH of this composition is 6.3.

After crimping, 9.5 g of a 43/57 mixture of dichlorotetrafluoroethane and dichlorodifluoromethane are introduced through the valve.

0.3 g of basic aluminium chloride and 0.15 g of powdered sodium carbonate are introduced into the chamber 5.

The powder present in the chamber 5 has the following characteristics:

particle diameter of between 0.09 mm and 0.5 mm;

more than 80% by weight of the particles have a diameter of between 0.15 mm and 0.4 mm.

A retention plug identical with that of Example 4 is placed against the grid 6.

This device makes it possible to deliver directly onto 90% white hair a foam which is left to act for 10 minutes, after which a water rinse is applied.

After washing, rinsing and drying, the yellowing white hair is tinted to a de-yellowing bluish-grey shade.

EXAMPLE 7

A product for treating psoriasis of the scalp is prepared as indicated below:

50 g of the following composition are introduced into the container 1 of the device:

| | |
|---|---|
| Mixture of monoisopropanolamine lauryl ether sulphate and of copra diethanolamide (marketed by the Henkel company under the trade name "Texapon WW 99") | 40 g |
| Liquid paraffin | 20 g |
| Preservative, perfume | q.s. |
| Mixture of triglycerides of saturated $C_8$–$C_{12}$ fatty acids (marketed by the Dynamit Nobel company under the trade name "Miglyol 812" | q.s. 100 g |

After the valve cup has been crimped onto the container, 15 g of a ternary butane/isobutane/propane mixture containing at least 55% by weight of isobutane and having a vapour pressure of 3.2 bars at 20° C. are introduced through the valve, this mixture being marketed by the Elf-Aquitaine company under the trade name "Aerogaz 3.2 N".

1 g of anthralin in the form of micronized powder is introduced into the chamber 5, the particle sizes of the powder having the following characteristics:

particle diameter of between 0.01 mm and 0.06 mm;

more than 80% of the particles have a diameter of between 0.015 and 0.04 mm.

As shown in FIGS. 2 and 3, against the grid is placed a retaining plug consisting of a cloth woven of fibres of the polyamide known under the commercial designation "nylon", said filaments having a diameter of about 35 microns and being woven with a mesh size of from 50 to 80 microns to constitute a cloth having a weight of 25 g/m² and a thickness of about 70 microns.

This device makes it possible to deliver directly onto wet hair a foam with which the hair and the scalp are impregnated. This is left to act for 20 min and is followed by rinsing with water and then by drying. A treatment for psoriasis of the scalp is thus performed with the aid of a shampoo which is easy to rinse off. Since the active substance and the surfactants are delivered separately, no problem of chemical incompatibility arises.

EXAMPLE 8

A shampoo for treating psoriasis of the scalp is prepared as follows:

50 g of the following composition are placed in the container 1 of the device according to the invention:

| | |
|---|---|
| Mixture of monoisopropanolamine lauryl ether sulphate and of copra diethanolamide (marketed by the Henkel company under the trade name "Texapon WW 99") | 35 g |
| Liquid paraffin | 15 g |
| Petroleum jelly | 5 g |
| Lauryl alcohol polyoxyethylenated with 4 moles of ethylene oxide (marketed by the Atlas company under the trade name "Brij 30") | 5 g |
| Preservative, perfume | q.s. |
| Sunflower oil | q.s. 100 g |

After the valve cup has been crimped, 30 g of the ternary butane/isobutane/propane mixture defined in Example 7, or of a 30/70 mixture of trichlorofluoromethane and 1,2-dichloro-1,1,2,2-tetrafluoroethane, are introduced through the valve.

1 g of hydrocortisone is introduced into the chamber 5. The hydrocortisone may be replaced with another corticoid, fluorinated or otherwise, for example with 0.2 g of β-methasone or with 0.1 g of hydrocortisone 17-ester, associated or otherwise with a keratolytic agent, for example 1 g of salicylic acid. This component, which is present in chamber 5, is in the form of a powder whose characteristics are as follows:

particle diameter between 0.005 and 0.015 mm;

more than 80% of the particles have a diameter of between 0.005 and 0.01 mm.

Against the grid is placed a retaining plug consisting of a cloth woven of filaments of the polyamide known under the commercial designation "nylon", said filaments having a diameter of about 7 microns and being woven with a mesh size of around 10 microns to form a cloth having a weight of about 65 g/m² and a thickness of about 15 microns.

This device makes it possible to deliver directly onto wet hair a foam with which the hair and the scalp are impregnated. This is left to act for 20 min and is rinsed off with water and this is then followed by drying. A treatment for psoriasis of the scalp is thus carried out with the aid of a shampoo whose active substance, suspended in the foaming excipient, does not settle out in the container 1. In addition, this application makes it possible to combine a neutral shampoo with a corticoid, while the preferred pH for obtaining good stability of the corticoid lies between 3.5 and 5.5.

EXAMPLE 9

A foaming oil for treating psoriasis of the scalp is prepared as indicated below.

80 g of the following composition are placed in the container 1 of the device according to the invention:

| | |
|---|---|
| Mixture of monoisopropanolamide lauryl ether sulphate and of copra diethanolamide (marketed by the Henkel company under the trade name "Texapon WW 99") | 35 g |
| Liquid paraffin | 23.9 g |
| Refined rapeseed oil | 40.8 g |
| Propyl para-hydroxybenzoate | 0.3 g |

After the valve cup has been crimped on, 20 g of the ternary butane/isobutane/propane mixture defined in Example 7 are introduced through the valve.

0.2 g of anthralin is introduced into the chamber 5 in the form of a powder, whose characteristics are as follows:

particle diameter of between 0.01 and 0.07 mm;

more than 80% of the particles have a diameter of between 0.015 and 0.04 mm.

A retaining plug identical with that of Example 7 is placed against the grid.

This device makes it possible to deliver directly onto wet hair a foam with which the hair and the scalp are impregnated. This is left to act for 20 minutes and is rinsed off with water and this is followed by drying. An effective treatment for psoriasis of the scalp is thus performed.

EXAMPLE 10

An antidandruff shampoo is prepared by introducing the following composition into the container 1 of the device according to the invention:

| | |
|---|---|
| Nonionic surfactant produced according to French Patent 2,091,516 by condensing 3.5 moles of glycidol with a $C_{11}$-$C_{14}$ α-diol | 5.0 g |
| Sorbitan monolaurate polyoxyethylenated with 20 moles of ethylene oxide, sold under the trade name "Tween 20" by the Atlas company | 5.0 g |
| Polymethacrylic acid with a molecular weight of approximately 26,000, sold at 20% strength of active substances under the trade name "Versicol K 13" by the Allied Colloids company: as active substances | 3.5 g |
| NaOH | q.s. pH 7.5 |
| Quaternary polyvinylpyrrolidone copolymer with a molecular weight of 1,000,000, sold at 20% strength of active substances under the trade name "Gafquat 755" by the General Aniline company: as active substances | 0.7 g |
| Perfume, preservative | q.s. |
| Water | q.s. 100.0 g |

After crimping, 10 g of a 70/30 mixture of dichlorotetrafluoroethane and dichlorodifluoromethane are introduced through the valve.

The chamber 5 contains 0.5 g of powdered ethanolamine salt of 1-hydroxy-4-methyl-6-(2,4,4-trimethylpentyl)-2(1H)pyridinone, sold under the trade name "Octopirox" by the Hoechst company.

The powder present in chamber 5 has the following characteristics:

particle diameter of between 0.1 and 0.5 mm;

more than 80% by weight of the particles have a diameter of between 0.2 and 0.5 mm.

A retaining plug identical with that of Example 4 is placed against the grid 6. This device makes it possible to deliver an antidandruff foam shampoo directly onto hair.

I claim:

1. A device for preparing and dispensing a product consisting of first and second components which may be mixed only when the product is being dispensed, said first component being fluid and able to constitute a foam, and said second component being solid, comprising:
   (a) a pressurized container containing said first component in the form of a liquid;
   (b) an outlet valve of said pressurized container through which the first component is to be dispensed;
   (c) an operating device for said outlet valve;
   (d) means defining an ejection duct from said outlet valve; said ejection duct having a first end nearer said outlet valve and a second end remote from said outlet valve, the second end of said ejection duct delivering the first component in the form of foam;
   (e) a chamber having an inlet connected to said second end of said ejection duct and an outlet, said chamber enclosing said second component in particulate form and maintaining it outside the said pressurized container; and
   (f) said device consisting of a single grid closing said outlet of said chamber;
   said device including a retaining plug separating said second, solid component from said grid.

2. A device according to claim 1, wherein the grid has from 6 to 100 meshes per centimeter, with a mesh opening of from 0.1 to 1.5 mm, whereby the foam emerging from the container has a compactness index (as hereinbefore defined) of from 3 to 60 s and is discharged into the chamber so as to produce on the grid an output of from 0.8 to 3 g/cm$^2$/s.

3. A device according to claim 2, wherein the compactness index (as hereinbefore defined) of the foam is from 3 to 40 s and the flow rate of foam on the grid is from 1 to 2 g/cm$^2$/s.

4. A device according to claim 1, wherein said chamber includes a side wall which widens gradually outwards from the ejection duct towards the grid.

5. A device according to claim 1, wherein the chamber is mounted removably on the end of the ejection duct.

6. A device according to claim 1, wherein the chamber is integrally fastened to the operating device.

7. A device according to claim 1, wherein more than 80% of the particles of said second component have a mean diameter of from 0.005 to 1.0 mm.

8. A device according to claim 1, wherein the retaining plug is a plug which is insoluble in said first component, said plug being permeable to the said first component and having a specific density of from 20 to 150 kg/m$^3$.

9. A device according to claim 1, wherein the plug is a non-woven fibrous plug.

10. A device according to claim 1, wherein the pressurized container contains a propellant gas consisting of at least one alkane taken from the group consisting of propane, butane, isobutane, mixtures thereof, and at least one halogenated hydrocarbon.

11. A device according to claim 1, wherein said first component is one of a dyeing composition and a hair shampoo composition and said second component is a powder of at least one oxidizing compound.

12. A device according to claim 1, wherein said first component is a solution of cosmetic polymer, and said second component is one of the group comprising a mono-methylol of urea, a dimethylol of urea, a monomethylol of thiourea, a dimethylol of thiourea, and derivatives thereof, and is capable of being used as a hair restructuring agent.

13. A device according to claim 1, wherein said first component is a solution of hair dyes and that said second component is one of a mordanting and an oxidation product.

14. The device as claimed in claim 1 wherein the plug is an open-cell plastic foam.

* * * * *